(12) United States Patent
Spurr et al.

(10) Patent No.: US 12,221,420 B2
(45) Date of Patent: Feb. 11, 2025

(54) PROCESS FOR THE PREPARATION OF SUBSTITUTED PYRAZOLE DERIVATIVES

(71) Applicant: Hoffmann-La Roche Inc., Little Falls, NJ (US)

(72) Inventors: Paul Spurr, Riehen (CH); Rene Trussardi

(73) Assignee: Hoffmann-La Roche Inc., Little Falls, NJ (US)

( * ) Notice: Subject to any disclaimer, the term of this patent is extended or adjusted under 35 U.S.C. 154(b) by 617 days.

(21) Appl. No.: 17/571,182

(22) Filed: Jan. 7, 2022

(65) Prior Publication Data

US 2022/0127236 A1  Apr. 28, 2022

Related U.S. Application Data

(63) Continuation of application No. PCT/EP2020/069317, filed on Jul. 9, 2020.

(30) Foreign Application Priority Data

Jul. 11, 2019  (EP) ..................................... 19185640
Sep. 2, 2019  (EP) ..................................... 19194896

(51) Int. Cl.
*C07D 231/14* (2006.01)

(52) U.S. Cl.
CPC .................................. *C07D 231/14* (2013.01)

(58) Field of Classification Search
CPC ................................................... C07D 231/14
See application file for complete search history.

(56) References Cited

FOREIGN PATENT DOCUMENTS

WO   2015/050798 A1   9/2015
WO   2017/157873 A1   9/2021

OTHER PUBLICATIONS

International Preliminary Report on Patentability—PCT/EP2020/069317 issued Jan. 11, 2022.
International Search Report for PCT/EP2020/069317 mailed Oct. 14, 2020; pp. 1-12.
Skinner, P. et al., "Fluorinated pyrazole acids are agonists of the high affinity niacin receptor GPR1O9a" Bioorg. Med. Chem. Lett. 17:5620-5623 (2007).

*Primary Examiner* — Timothy R Rozof
(74) *Attorney, Agent, or Firm* — Bradley E. Davis

(57) ABSTRACT

The invention provides a process for manufacturing 5-ethyl-4-methyl-N-[4-[(2S) morpholin-2-yl]phenyl]-1H-pyrazole-3-carboxamide (Formula I), or a pharmaceutically acceptable salt thereof, on an industrial scale,

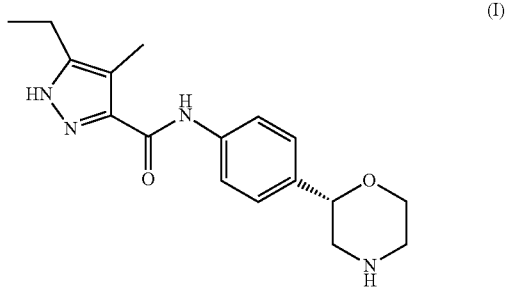

comprising a one-pot process for manufacturing 5-ethyl-4-methyl-1H-pyrazole-3-carboxylic acid (1).

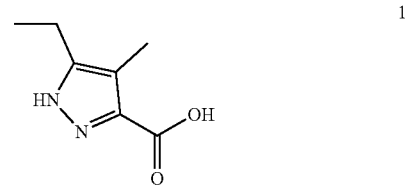

20 Claims, No Drawings

PROCESS FOR THE PREPARATION OF SUBSTITUTED PYRAZOLE DERIVATIVES

CROSS-REFERENCE TO RELATED APPLICATIONS

This application is a continuation of International Application No. PCT/EP2020/069317 having an International filing date of Jul. 9, 2020, which claims benefit of and priority to European Patent Application No. 19185640.0, filed Jul. 11, 2019, and European Patent Application No. 19194896.7, filed Sep. 2, 2019, the contents of which are incorporated herein by reference in their entirety.

FIELD OF THE INVENTION

The invention relates to a novel process for manufacturing 5-ethyl-4-methyl-N-[4-[(2S) morpholin-2-yl]phenyl]-1H-pyrazole-3-carboxamide (Formula I), or a pharmaceutically acceptable salt thereof.

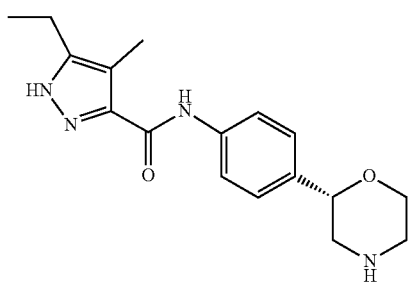

I

BACKGROUND OF THE INVENTION

The compound of Formula I is a TAAR1 inhibitor useful for the treatment of various diseases and disorders, such as depression, anxiety disorders, bipolar disorder, attention deficit hyperactivity disorder (ADHD), stress-related disorders, schizophrenia, Parkinson's disease, Alzheimer's disease, epilepsy, migraine, hypertension, substance abuse, addiction, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders (PCT application WO2017157873).

WO2017157873 discloses a process for making the compound of formula I, comprising reacting a 5-ethyl-4-methyl-1H-pyrazole-3-carboxylic acid (1) with (2S)-2-(4-aminophenyl)morpholine-4-carboxylate (2) to form tert-Butyl (2S)-2-[4-[(5-ethyl-4-methyl-1H-pyrazole-3-carbonyl)amino]phenyl]morpholine-4-carboxylate (3).

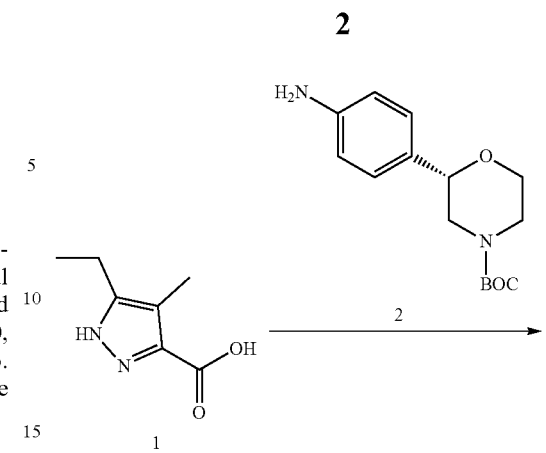

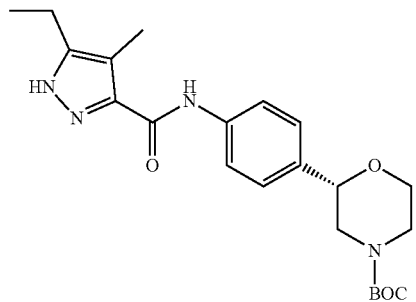

(2S)-2-(4-aminophenyl)morpholine-4-carboxylate (2) may be obtained as described e.g. in PCT application WO2015086495.

5-ethyl-4-methyl-1H-pyrazole-3-carboxylic acid (1) may be obtained as described e.g. in Philip J. Skinner et al., *Bioorg. Med. Chem. Lett.* 2007, 17, 5620-5623.

For marketing products, it is necessary to produce pharmaceuticals in large quantities and according to good manufacturing practice ("GMP"). Hence, high-yielding, cheap and reproducible syntheses are of utmost importance.

The synthesis of 5-ethyl-4-methyl-1H-pyrazole-3-carboxylic acid (1) described in Skinner et al. has several drawbacks, such as low yield and high reaction temperatures, which ultimately impact the industrial scale synthesis of the compound of formula I according to the procedure described in WO2017157873.

Therefore, there is a need for a new process for manufacturing the compound of formula (I), or a pharmaceutically acceptable salt thereof.

SUMMARY OF THE INVENTION

In a first aspect, the present invention provides a process for manufacturing 5-ethyl-4-methyl-N-[4-[(2S) morpholin-2-yl]phenyl]-1H-pyrazole-3-carboxamide (Formula I), or a pharmaceutically acceptable salt thereof,

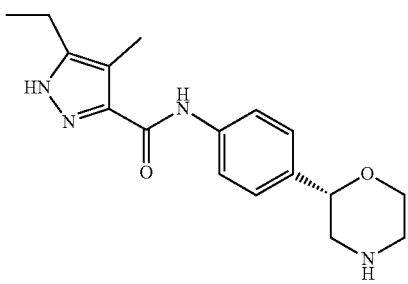

I comprising:
a) reacting pentan-3-one (4),

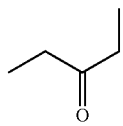

4 with a dialkyl or diaryl oxalate 5, wherein R is $C_1$-$C_6$-alkyl or $C_6$-$C_{14}$-aryl, in the presence of a base;

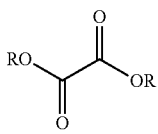

5 b) adding (i) hydrazine hydrate in the presence of an acid, such as acetic acid or hydrochloric acid or (ii) a hydrazine salt, such as hydrazine acetate or hydrazine hydrochloride, to the reaction mixture obtained from step a);

c) adding an aqueous solution of an alkali metal hydroxide to the mixture obtained from step b); and d) adjusting the pH of the mixture obtained from step c) to below pH 6 by adding an acid;

to form 5-ethyl-4-methyl-1H-pyrazole-3-carboxylic acid (1)

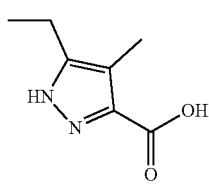

1 wherein steps a)-d) are performed without isolation of any intermediates.

In a further aspect, the present invention provides a process for manufacturing 5-ethyl-4-methyl-1H-pyrazole-3-carboxylic acid (1)

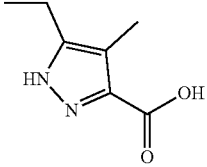

1 comprising:
a) reacting pentan-3-one (4),

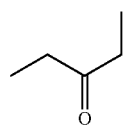

4 with a dialkyl or diaryl oxalate 5, wherein R is $C_1$-$C_6$-alkyl or $C_6$-$C_{14}$-aryl, in the presence of a base;

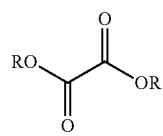

5 b) adding (i) hydrazine hydrate in the presence of an acid, such as acetic acid or hydrochloric acid or (ii) a hydrazine salt, such as hydrazine acetate or hydrazine hydrochloride, to the reaction mixture obtained from step a);

c) adding an aqueous solution of an alkali metal hydroxide to the mixture obtained from step b); and d) adjusting the pH of the mixture obtained from step c) to below pH 6 by adding an acid;

to form said 5-ethyl-4-methyl-1H-pyrazole-3-carboxylic acid (1);

wherein steps a)-d) are performed without isolation of any intermediates.

In a further aspect, the present invention provides the use of the one-pot process for the manufacture of 5-ethyl-4-methyl-1H-pyrazole-3-carboxylic acid (1) described herein for the manufacture of 5-ethyl-4-methyl-N-[4-[(2S) morpholin-2-yl]phenyl]-1H-pyrazole-3-carboxamide (Formula I), or a pharmaceutically acceptable salt thereof.

In a further aspect, the present invention provides 5-ethyl-4-methyl-N-[4-[(2S) morpholin-2-yl]phenyl]-1H-pyrazole-3-carboxamide (Formula I), or a pharmaceutically acceptable salt thereof, when obtained by the processes described herein.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims and the abstract), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims and the abstract), or to any novel one, or any novel combination, of the steps of any method or process so disclosed.

The term "alkyl" refers to a monovalent, linear or branched saturated hydrocarbon group of 1 to 6 carbon atoms ("$C_{1-6}$-alkyl"), e.g. 1, 2, 3, 4, 5, or 6 carbon atoms. In other embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is ethyl.

The term "aryl" refers to a monocyclic, bicyclic, or tricyclic carbocyclic ring system having a total of 6 to 14 ring members ("$C_{6-14}$-aryl"), preferably, 6 to 12 ring members, and more preferably 6 to 10 ring members, and wherein at least one ring in the system is aromatic. A preferred, yet non-limiting example of aryl is phenyl.

The term "base" refers to bases that are suitable for use in Claisen condensations, such as alkoxides, hydrides or dialkylazanides. Particular examples of bases are sodium or potassium methoxide, sodium or potassium ethoxide, sodium or potassium tert-butoxide, lithium diisopropylamide (LDA), and sodium or potassium hydride. Preferred examples of bases are sodium ethoxide, sodium methoxide, and potassium tert-butoxide. A particularly preferred example of a base is sodium methoxide.

The term "acid" refers to a compound having at least one acidic proton. Particular, yet non-limiting examples of acids are hydrochloric acid and acetic acid.

Manufacturing Processes

The present invention concerns a process for manufacturing 5-ethyl-4-methyl-N-[4-[(2S) morpholin-2-yl]phenyl]-1H-pyrazole-3-carboxamide (Formula I), or a pharmaceutically acceptable salt thereof,

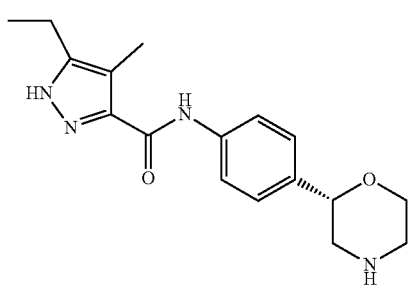

I comprising a one pot process for manufacturing 5-ethyl-4-methyl-1H-pyrazole-3-carboxylic acid (1)

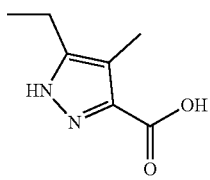

1 as outlined in Scheme 1.

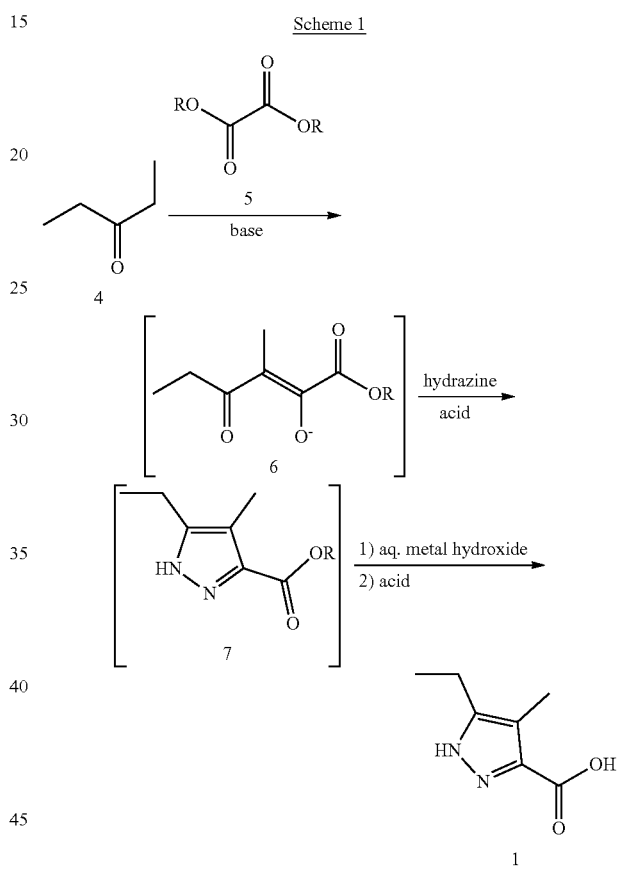

According to the one-pot process of the invention, a Claisen condensation of pentan-3-one (4) with a dialkyl or diaryl oxalate 5, wherein R is $C_1$-$C_6$-alkyl or $C_6$-$C_{14}$-aryl, preferably with diethyl oxalate, in the presence of a base, such as an alkali metal alkoxide, in particular sodium ethoxide, affords intermediate 6, which is reacted with hydrazine in the presence of an acid, more particularly with a hydrazine salt such as hydrazine hydrochloride or hydrazine acetate (also formed in situ from the individual components), to afford carboxylic acid ester 7. Subsequently, carboxylic acid ester 7 is saponified by adding an aqueous solution of an alkali metal hydroxide, such as LiOH, NaOH or KOH, in particular NaOH, directly to the reaction mixture obtained from the cyclization step. 5-Ethyl-4-methyl-1H-pyrazole-3-carboxylic acid (1) is finally achieved by acidifying (pH<7, in particular pH<3, preferably pH=2.0-2.5) the reaction mixture, e.g. by adding aqueous hydrochloric acid.

One of the surprising advantages of one pot process for manufacturing 5-ethyl-4-methyl-1H-pyrazole-3-carboxylic acid (1) described herein is that it results in higher yields than e.g. the process disclosed in Philip J. Skinner et al., *Bioorg. Med. Chem. Lett.* 2007, 17, 5620-5623 (i.e., 75% vs. 26%).

In a first aspect, the present invention provides a process for manufacturing 5-ethyl-4-methyl-N-[4-[(2S) morpholin-2-yl]phenyl]-1H-pyrazole-3-carboxamide (Formula I), or a pharmaceutically acceptable salt thereof,

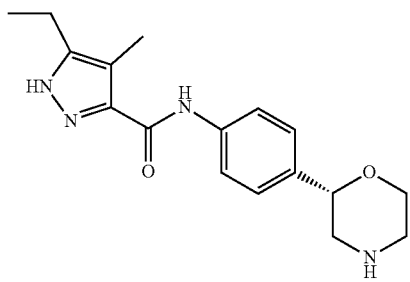

I comprising:
a) reacting pentan-3-one (4),

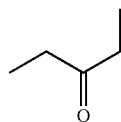

4 with a dialkyl or diaryl oxalate 5, wherein R is $C_1$-$C_6$-alkyl or $C_6$-$C_{14}$-aryl, in the presence of a base;

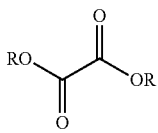

5 b) adding (i) hydrazine hydrate in the presence of an acid, such as acetic acid or hydrochloric acid or (ii) a hydrazine salt, such as hydrazine acetate or hydrazine hydrochloride, to the reaction mixture obtained from step a);
c) adding an aqueous solution of an alkali metal hydroxide to the mixture obtained from step b); and
d) adjusting the pH of the mixture obtained from step c) to below pH 6 by adding an acid;
to form 5-ethyl-4-methyl-1H-pyrazole-3-carb oxylic acid (1)

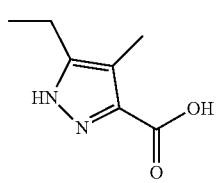

1 wherein steps a)-d) are performed without isolation of any intermediates.

In a further aspect, the present invention provides a process for manufacturing 5-ethyl-4-methyl-1H-pyrazole-3-carboxylic acid (1)

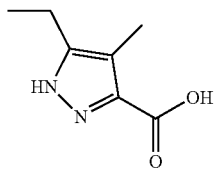

1 comprising:
a) reacting pentan-3-one (4),

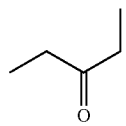

4 with dialkyl or diaryl oxalate 5, wherein R is $C_1$-$C_6$-alkyl or $C_6$-$C_{14}$-aryl, in the presence of a base;

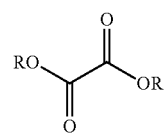

5 b) adding (i) hydrazine hydrate in the presence of an acid, such as acetic acid or hydrochloric acid or (ii) a hydrazine salt, such as hydrazine acetate or hydrazine hydrochloride, to the reaction mixture obtained from step a);
c) adding an aqueous solution of an alkali metal hydroxide to the mixture obtained from step b); and
d) adjusting the pH of the mixture obtained from step c) to below pH 6 by adding an acid;
to form said 5-ethyl-4-methyl-1H-pyrazole-3-carboxylic acid (1);
wherein steps a)-d) are performed without isolation of any intermediates.

In one embodiment, more than 1 equivalent of pentan-3-one (4) is used in step a) relative to dialkyl or diaryl oxalate 5.

In a preferred embodiment, about 1 equivalent to about 2 equivalents of pentan-3-one (4) are used in step a) relative to dialkyl or diaryl oxalate 5.

In a particularly preferred embodiment, about 1 equivalent to about 1.5 equivalents, e.g. about 1.2 equivalents of pentan-3-one (4) are used in step a) relative to dialkyl or diaryl oxalate 5.

In one embodiment, the oxalate 5 in step a) of the process of the invention is a dialkyl oxalate, wherein R is $C_1$-$C_6$-alkyl.

In one embodiment, the oxalate 5 in step a) of the process of the invention is diethyl oxalate.

In one embodiment, the base in step a) of the process of the invention is an alkali metal alkoxide.

In a preferred embodiment, the base in step a) of the process of the invention is sodium ethoxide.

In one embodiment, about 1 equivalent to about 2 equivalents of base are used in step a) relative to dialkyl or diaryl oxalate 5.

In a preferred embodiment, about 1 equivalent to about 1.5 equivalents of base are used in step a) relative to dialkyl or diaryl oxalate 5.

In a particularly preferred embodiment, about 1 equivalent to about 1.1 equivalents of base are used in step a) relative to dialkyl or diaryl oxalate 5.

In one embodiment, step a) is conducted below 75° C., e.g. between about 0° C. and about 25° C.

In a preferred embodiment, step a) is conducted between about 0° C. and about 10° C.

In a particularly preferred embodiment, step a) is conducted between about 0° C. and about 5° C.

In one embodiment, in step b) of the process of the invention, a hydrazine salt selected from the group consisting of hydrazine hydrochloride ($N_2H_4 \cdot HCl$) and hydrazine acetate ($N_2H_4 \cdot CH_3COOH$), each as is, or formed in situ, is used.

In a preferred embodiment, in step b) of the process of the invention, hydrazine acetate ($N_2H_4 \cdot CH_3COOH$) as is, or formed in situ, is used.

In one embodiment, about 0.95 equivalents to about 1.5 equivalents of hydrazine or hydrazine salt relative to dialkyl or diaryl oxalate 5 are used in step b).

In a preferred embodiment, about 0.95 equivalents to about 1.1 equivalents of hydrazine or hydrazine salt relative to dialkyl or diaryl oxalate 5 are used in step b).

In a particularly preferred embodiment, <1 equivalent, e.g. about 0.95 equivalents, of hydrazine or hydrazine salt relative to diester 5 are used in step b).

It has been found that in some instances, using <1 equivalent hydrazine relative to diester 5 in step b) beneficially reduces the level of contamination by the hydrazide derivative of the desired product in 5-ethyl-4-methyl-1H-pyrazole-3-carboxylic acid (1).

In one embodiment, step b) is conducted below about 5° C.

In a preferred embodiment, step b) is conducted below about 0° C.

In a particularly preferred embodiment, step b) is conducted between about −15° C. and about 0° C.

In one embodiment of the process of the invention, the alkali metal hydroxide in step c) is LiOH, KOH or NaOH.

In a preferred embodiment of the process of the invention, the alkali metal hydroxide in step c) is NaOH.

In one embodiment, about 2 equivalents to about 4 equivalents of alkali metal hydroxide relative to dialkyl or diaryl oxalate 5 are used in step c).

In a preferred embodiment, about 2 equivalents to about 3 equivalents of alkali metal hydroxide relative to dialkyl or diaryl oxalate 5 are used in step c).

In a particularly preferred embodiment, about 2.5 equivalents to about 2.9 equivalents, e.g. about 2.85 equivalents of alkali metal hydroxide relative to dialkyl or diaryl oxalate 5 are used in step c).

In one embodiment, step c) is conducted below 30° C., e.g. between about 0° C. and about 30° C.

In a preferred embodiment, step c) is conducted between about 0° C. and about 20° C.

In a particularly preferred embodiment, step c) is conducted between about 0° C. and about 15° C.

In one embodiment, the mixture obtained from step c) is stirred for an extended period of time (e.g., about 10 to about 20 h) at elevated temperature (e.g., about 40° C. to about 50° C.).

In one embodiment, step c) comprises adding an aqueous solution of an alkali metal hydroxide to the mixture obtained from step b) until the pH is ≥ about 12.5, e.g. about 14.

In one embodiment of the process of the invention, in step d), the pH of the mixture obtained from step c) is adjusted to between about pH 1.5 and about pH 5.

In a preferred embodiment of the process of the invention, in step d), the pH of the mixture obtained from step c) is adjusted to between about pH 1.5 and about pH 3.

In a particularly preferred embodiment of the process of the invention, in step d), the pH of the mixture obtained from step c) is adjusted to between about pH 2.0 and about pH 2.5.

In one embodiment of the process of the invention, the acid added in step d) is hydrochloric acid.

In one embodiment, the acid in step d) is added at about 0° C. to about 60° C.

In a preferred embodiment, the acid in step d) is added at about 40° C. to about 50° C.

In a particularly preferred embodiment, the acid in step d) is added at about 45° C.

In one embodiment, the present invention provides a process for manufacturing 5-ethyl-4-methyl-N-[4-[(2S)morpholin-2-yl]phenyl]-1H-pyrazole-3-carboxamide (Formula I), or a pharmaceutically acceptable salt thereof, or a process for manufacturing 5-ethyl-4-methyl-1H-pyrazole-3-carboxylic acid (1) as described herein, comprising:

a) reacting pentan-3-one (4, more than 1 equivalent with respect to dialkyl oxalate 5),

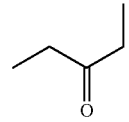

4 with a dialkyl oxalate 5, wherein R is $C_1$-$C_6$-alkyl (1.00 equivalent) in the presence of a base (about 1 equivalent to about 2 equivalents) at below 75° C., e.g. between about 0° C. and about 25° C.;

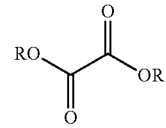

5 b) adding about 0.95 equivalents to about 1.5 equivalents with respect to 5 of (i) hydrazine hydrate in the presence of an acid, such as acetic acid or hydrochloric acid or (ii) a hydrazine salt, such as hydrazine acetate or hydrazine hydrochloride, to the reaction mixture obtained from step a) at below about 5° C.;

c) adding an aqueous solution of an alkali metal hydroxide (about 2 equivalents to about 4 equivalents with respect to 5) to the mixture obtained from step b) at a temperature below about 30° C.; and d) adjusting the pH of the mixture obtained from step c) to between about pH 1.5 and about pH 5 by adding an acid at about 0° C. to about 60° C.;

to form 5-ethyl-4-methyl-1H-pyrazole-3-carboxylic acid (1).

In a preferred embodiment, the present invention provides a process for manufacturing 5-ethyl-4-methyl-N-[4-[(2S) morpholin-2-yl]phenyl]-1H-pyrazole-3-carboxamide (Formula I), or a pharmaceutically acceptable salt thereof, or a process for manufacturing 5-ethyl-4-methyl-1H-pyrazole-3-carboxylic acid (1) as described herein, comprising:

a) reacting pentan-3-one (4, about 1 equivalent to about 2 equivalents with respect to 5),

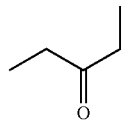

with a dialkyl oxalate 5, wherein R is $C_1$-$C_6$-alkyl (1.00 equivalent) in the presence of a base (about 1 equivalent to about 1.5 equivalents) at between about 0° C. and about 10° C., wherein the base is an alkali metal alkoxide;

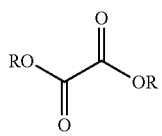

b) adding about 0.95 equivalents to about 1.1 equivalents with respect to 5 of a hydrazine salt to the reaction mixture obtained from step a), keeping the temperature below about 0° C., wherein the hydrazine salt is hydrazine hydrochloride ($N_2H_4 \cdot HCl$) or hydrazine acetate ($N_2H_4 \cdot CH_3COOH$), as is, or formed in situ;

c) adding an aqueous solution of an alkali metal hydroxide (about 2 equivalents to about 3 equivalents with respect to 5) to the mixture obtained from step b) at a temperature below about 20° C., wherein the alkali metal hydroxide is LiOH, KOH or NaOH; and d) adjusting the pH of the mixture obtained from step c) to between about pH 1.5 and about pH 3 by adding an acid at about 0° C. to about 60° C.;

to form 5-ethyl-4-methyl-1H-pyrazole-3-carboxylic acid (1).

In a particularly preferred embodiment, the present invention provides a process for manufacturing 5-ethyl-4-methyl-N-[4-[(2S) morpholin-2-yl]phenyl]-1H-pyrazole-3-carboxamide (Formula I), or a pharmaceutically acceptable salt thereof, or a process for manufacturing 5-ethyl-4-methyl-1H-pyrazole-3-carboxylic acid (1) as described herein, comprising:

a) reacting pentan-3-one (4, about 1 equivalent to about 1.5 equivalents, e.g. about 1.2 equivalents, with respect to 5),

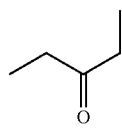

with diethyl oxalate 5a (1.00 equivalent) in the presence of sodium ethoxide or sodium methoxide, preferably sodium ethoxide (about 1.0 equivalent to about 1.1 equivalents) at about 0° C. to about 5° C.;

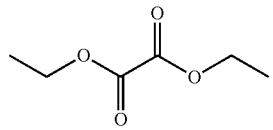

b) adding <1 equivalent, e.g. about 0.95 equivalents with respect to 5 of hydrazine acetate ($N_2H_4 \cdot CH_3COOH$), as is, or formed in situ to the reaction mixture obtained from step a), keeping the temperature below about 0° C.;

c) adding an aqueous solution of NaOH (about 2.5 equivalents to about 2.9 equivalents, e.g. about 2.85 equivalents with respect to 5) to the mixture obtained from step b), keeping the temperature at between about 0° C. and about 15° C.; and d) adjusting the pH of the mixture obtained from step c) to between about pH 2.0 and about pH 2.5 by adding hydrochloric acid at about 40° C. to about 50° C.;

to form 5-ethyl-4-methyl-1H-pyrazole-3-carboxylic acid (1).

In a further aspect, the present invention provides the use of the one-pot process for manufacturing 5-ethyl-4-methyl-1H-pyrazole-3-carboxylic acid (1) described herein for manufacturing 5-ethyl-4-methyl-N-[4-[(2S) morpholin-2-yl]phenyl]-1H-pyrazole-3-carboxamide (Formula I), or a pharmaceutically acceptable salt thereof.

In a further aspect, the present invention provides 5-ethyl-4-methyl-N-[4-[(2S) morpholin-2-yl]phenyl]-1H-pyrazole-3-carboxamide (Formula I), or a pharmaceutically acceptable salt thereof, when obtained by the processes described herein.

EXAMPLES

The invention will be more fully understood by reference to the following examples. The claims should not, however, be construed as limited to the scope of the examples.

All reactions were performed under a protective gas atmosphere (e.g. argon or nitrogen) if not specified otherwise.

Example 1

5-ethyl-4-methyl-1H-pyrazole-3-carboxylic acid (1)

3-Pentanone (93.0 g, 1.08 mol, 1.20 eq) was added to a maintained precooled (−5-0° C.) solution of diethyl oxalate (132 g, 903 mmol, 1.00 eq) in 20% ethanolic sodium ethoxide (338 g, 994 mmol, 1.10 eq). The line was rinsed with ethanol (50 mL). After stirring 2 h at this temperature, the reaction mixture was cooled to ca. −15° C. and a cold (ca. 0° C.) solution of 40% aqueous hydrazine (118 g, 948 mmol, 1.05 eq) in acetic acid (59.7 g, 994 mmol, 1.10 eq) was added dropwise over 2 h ensuring the reaction temperature did not exceed 0° C. Stirring was continued for 1 h. Keeping the internal temperature between 0 and 15° C., a 50% aqueous solution of sodium hydroxide (205 g, 2.57 mol, 2.85 eq) was added. The solension was stirred at 20±5° C. for 2 h, then at 40±5° C. for 16 h, resulting in the formation of a clear solution. Concentrated (37%) aqueous hydrochloric acid (350 mL, 3.68 mol, 4.07 eq) was added at 45±5° C. and the suspension arising was stirred for 0.5 h. The bulk of the organic solvent (ca. 475 mL ethanol) was removed under reduced pressure at 45±5° C. Water (475 mL) was added and the concoction was stirred at 45±5° C. for 1 h. The precipitate was filtered and washed with water (100 mL). The crude product was taken up in water (650 mL) and the pH was adjusted to 7.5-8 by the addition of 50% aqueous NaOH (65 g). After stirring the mixture at ambient temperature for 1 h, celite (25 g) was added and the bound insoluble material was removed by filtration. The filter cake was rinsed with water (150 mL) and the filtrate collected was warmed and sustained at 40-45° C. while being acidified to pH 2-2.5 by the addition of 37% aqueous HCl (82 mL). The resulting suspension was stirred at 40-45° C. for 1 h, filtered and the residue was washed with water (200 mL). The product was slurried once more in water (650 mL) at 35-40° C. for 1 h to remove by dissolution the last traces of residual oxalic acid. Following filtration, washing with water (200 mL) and drying (<45° C. under vacuum), the title compound was obtained as an off-white solid (108 g, 78% yield).

Elemental Analysis for $C_7H_{10}N_2O_2$ (154.17) calc.: C: 54.54%, H: 6.54%, N: 18.17%; found: C: 54.73, H: 6.53, N: 18.31; water content (Karl Fisher titration): <0.1%.

What is claimed is:

1. A method for preparing 5-ethyl-4-methyl-1H-pyrazole-3-carboxylic acid (1)

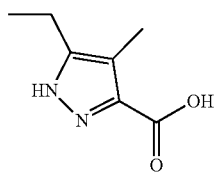

without isolation of intermediates,
said method comprising:
a) reacting in the presence of a base pentan-3-one (4),

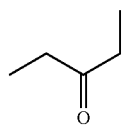

with a dialkyl or diaryl oxalate 5,

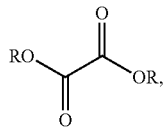

wherein R is $C_1$-$C_6$-alkyl or $C_6$-$C_{14}$-aryl;
b) adding (i) a hydrazine hydrate in the presence of an acid, or (ii) a hydrazine salt to the reaction mixture obtained from step a);
c) adding an aqueous solution of an alkali metal hydroxide to the mixture obtained from step b); and d) adjusting the pH of the mixture obtained from step c) to below pH 6 by adding an acid.

2. The method according to claim 1, wherein the base in step a) is sodium ethoxide.

3. The method according to claim 1, wherein the oxalate 5 in step a) is a dialkyl oxalate, wherein R is $C_1$-$C_6$-alkyl.

4. The method according to claim 3, wherein the oxalate 5 in step a) is diethyl oxalate.

5. The method according to claim 1, wherein step a) is conducted at a temperature below 75° C.

6. The method according to claim 5, wherein step a) is conducted at a temperature of between about 0° C. and about 25° C.

7. The method according to claim 1, wherein hydrazine hydrate is added to the reaction mixture obtained from step a).

8. The method according to claim 1, wherein hydrazine hydrate is added to the reaction mixture obtained from step a) in the presence of acetic acid or hydrochloric acid.

9. The method according to claim 1, wherein a hydrazine salt is added to the reaction mixture obtained from step a).

10. The method according to claim 9, wherein the hydrazine salt is hydrazine acetate ($N_2H_4 \cdot CH_3COOH$) or hydrazine hydrochloride ($N_2H_4 \cdot HCl$).

11. The method according to claim 9, wherein the hydrazine salt is formed in situ.

12. The method according to claim 1, wherein step b) is conducted at a temperature of below about 5° C.

13. The method according to claim 12, wherein step b) is conducted at a temperature of between about 0° C. and about −15° C.

14. The method according to claim 1, wherein the alkali metal hydroxide in step c) is LiOH, KOH or NaOH.

15. The method according to claim 14, wherein the alkali metal hydroxide in step c) is NaOH.

16. The method according to claim 1, wherein step c) is conducted at a temperature of below about 30° C.

17. The method according to claim 16, wherein step c) is conducted at a temperature of between about 0° C. and about 15° C.

18. The method according to claim 1, wherein in step d), the pH of the mixture obtained from step c) is adjusted to below pH 3.

19. The method according to claim 18, wherein the acid added in step d) is hydrochloric acid.

20. A method for preparing 5-ethyl-4-methyl-N-[4-[(2S) morpholin-2-yl]phenyl]-1H-pyrazole-3-carboxamide (Formula I),

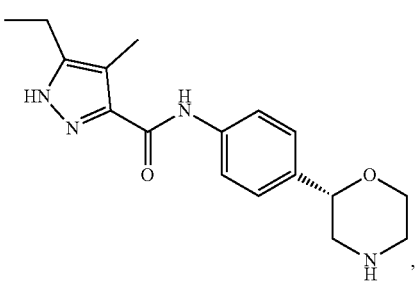

or a pharmaceutically acceptable salt thereof, said method comprising preparing 5-ethyl-4-methyl-1H-pyrazole-3-carboxylic acid (1)

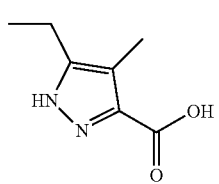
according to the method of claim 1.
* * * * *